United States Patent [19]

Vanlerberghe et al.

[11] 3,998,948
[45] Dec. 21, 1976

[54] SURFACE ACTIVE AGENT CONTAINING HYDROXYLATED ALKYLSULFINYL CHAINS AND COMPOSITION CONTAINING SURFACE ACTIVE AGENT HAVING HYDROXYLATED ALKYLTHIO AND/OR HYDROXYLATED ALKYLSULFINYL CHAINS

[75] Inventors: Guy Vanlerberghe, Montjay-la-Tour; Henri Sebag, Paris, both of France

[73] Assignee: L'Oreal, Paris, France

[22] Filed: June 6, 1975

[21] Appl. No.: 584,500

Related U.S. Application Data

[60] Division of Ser. No. 288,327, Sept. 12, 1972, Pat. No. 3,906,048, which is a continuation-in-part of Ser. No. 874,373, Nov. 5, 1969, abandoned.

[30] Foreign Application Priority Data

Nov. 5, 1968 Luxembourg .................. 57246

[52] U.S. Cl. .................. 424/170; 260/607 A; 260/607 E; 260/609 R; 424/70; 424/172; 252/171

[51] Int. Cl.² .................. A01N 9/04; A01N 17/10

[58] Field of Search ....... 260/607 A, 609 R, 607 E; 424/172, 70, 170; 252/171

[56] References Cited

UNITED STATES PATENTS

| | | | |
|---|---|---|---|
| 2,588,771 | 3/1952 | Schwartz | 260/609 R |
| 2,776,997 | 1/1957 | Doumani | 260/609 R |
| 2,926,118 | 2/1960 | Mahan | 260/607 AR |
| 3,427,248 | 2/1969 | Lamberti et al. | 260/609 F |
| 3,661,851 | 5/1972 | Umbach et al. | 260/609 F |
| 3,662,003 | 5/1972 | Umbach et al. | 260/609 R |
| 3,739,031 | 6/1973 | Priestley et al. | 260/607 AL |

FOREIGN PATENTS OR APPLICATIONS

175,958 12/1965 U.S.S.R. .................. 260/607 A

Primary Examiner—Lewis Gotts
Assistant Examiner—D. R. Phillips
Attorney, Agent, or Firm—Cushman, Darby & Cushman

[57] ABSTRACT

Compounds of the formula:

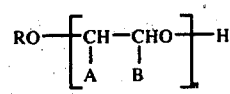

wherein R is alkyl, alkenyl, alkylaryl or alkylpolyoxyalkylene, $n$ is 1 – 20, one of A or B is hydrogen and the other is —CH₂Z where Z is (R'S-) or

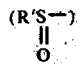

and where R' is alkyl or mono- or polyhydroxyalkyl. The compounds are obtained from compounds where —CH₂Z is replaced by chloromethyl or bromomethyl by reaction with mercaptan and, if necessary, oxidation of the sulfur. The compounds are useful in pharmaceutical, cosmetic and cleansing compositions.

9 Claims, No Drawings

SURFACE ACTIVE AGENT CONTAINING HYDROXYLATED ALKYLSULFINYL CHAINS AND COMPOSITION CONTAINING SURFACE ACTIVE AGENT HAVING HYDROXYLATED ALKYLTHIO AND/OR HYDROXYLATED ALKYLSULFINYL CHAINS

This is a continuation, division, of application Ser. No. 288,327 filed Sept. 12, 1972, U.S. Pat. No. 3,906,048 which is a continuation-in-part of Ser. No. 874,373, filed Nov. 5, 1969, now abandoned.

The present invention relates to a new product of manufacture comprising a chemical compound of the formula

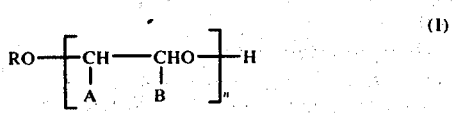

wherein R represents a member selected from the group consisting of linear or branched alkyl containing 8 – 30 carbon atoms, linear or branched alkenyl containing 8 – 30 carbon atoms, alkaryl containing 12 – 40 carbon atoms, alkyl polyoxyalkylene containing 14 – 60 carbon atoms and 1 – 10 oxygen atoms and cycloaliphatic radical containing 10 – 30 carbon atoms, one of A and B represents hydrogen and the other —CH$_2$Z wherein Z is selected from the group consisting of alkyl thio of the formula R'S- and alkyl sulfinyl of the formula

wherein R' is selected from the group consisting of alkyl having 1 – 4 carbon atoms, monohydroxyalkyl containing 1 – 4 carbon atoms and polyhydroxyalkyl containing 1 – 4 carbon atoms, and $n$ is a number between 1 – 20.

The present invention also relates to a process for the preparation of compounds of formula (I) using, as starting material, a polyhalogenated polyether of the formula:

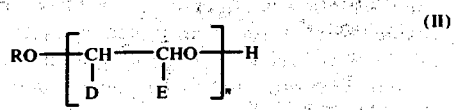

wherein R and n have the meanings given above in formula (I), one of D and E represents a hydrogen and the other a member selected from the group consisting of chloromethyl and bromomethyl, said process comprising the steps of condensing a mercaptan of formula R'SH with a polyether of formula (II) in an alkaline medium, R' having the meaning given above in formula (I), separating out the resulting alkaline halide that forms, and, where Z is

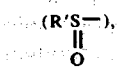

subjecting the thus obtained mixture to an oxidation treatment in aqueous solution.

The halogenated polyether starting material of formula (II) may be obtained by polyaddition of a glycerol epihalohydrin of formula:

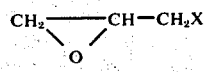

wherein X represents a member selected from the group consisting of chlorine and bromine, onto a hydroxyl compound of formula ROH in the presence of a Lewis acid catalyst such as boron trifluoride, stannic chloride or antimony pentachloride. If boron trifluoride is used as the catalyst, this substance is used in the proportion of 0.1 to 1% by weight of the total reaction mass, the reaction temperature being between 25° C and 160° C and preferably between 60° C and 120° C. In such a process, a mixture of compounds of formula (II) is obtained in which parameters n relating to each molecule are statistically distributed about an average value m called average degree of polymerization. It is quite clear that the process of preparation of the invention, whereby the compounds of formula (I) are obtained, starting from a mixture of compounds of formula (II) as indicated above, results in the production of a mixture of compounds of formula (I) which has the same characteristics as the starting mixture so far as distribution of parameters n about median value m is concerned.

An essential characteristic of the mixture of compounds of formula (I) of the invention is that the value m is between 1 and 10 inclusive. The present invention thus relates, as a new product of manufacture, to a mixture of compounds of formula (I) in which the meaning of symbols R, A and B are as indicated above, characterized in that its average degree of polymerization is between 1 and 10 inclusive.

In the process for preparing the compounds of formula (I) above, all the halogenated groups of the compound of formula (II) do not necessarily react with the mercaptan molecules, so that the products of formula (I) comprise a certain number of oxyalkylene units in which the halogen atom has been replaced by a sulfur containing radical, a certain number of oxyalkylene units in which the halogen atom has not reacted, and a certain number of oxyalkylene units in which the halogen atom has undergone hydrolysis and has been replaced by a hydroxyl group. One of the essential characteristics of the invention is, however, that at least 80%, preferably 90%, of the oxyalkylene units bear substituents comprising a sulfur atom.

In industrial type preparation, it is preferred to use polychlorinated polyethers, because of their low cost as compared to that of the polybrominated homologs, and because their good reactivity with mercaptans which allows the obtaining of excellent conversion efficiencies.

Among the mercaptans of the formula (R'SH) that can be used for synthesis of polythioethers and polysulfoxides in the formula (I), there can be mentioned: methyl mercaptan, 2-mercapto 1-ethanol, 1-mercapto 2-propanol, 3-mercapto; 1-propanol, 3-mercapto 1,2-propanediol, 1-mercapto; 2-butanol and 4-mercapto; 1,2-butanediol.

Among the (ROH) alcohols that serve as primary material in the production of polyhalogenated polyethers of the formula (II), there can be mentioned linear chain saturated alcohols with an even or uneven number of carbon atoms, especially 1-octanol, 1-decanol, 1-undecanol, 1-dodecanol, 1-tridecanol, 1-tetradecanol, 1-pentadecanol, 1-hexadecanol, 1-heptadecanol, 1-octodecanol, 1-eicosanol and 1-docosanol; linear chain unsaturated alcohols, especially oleic alcohol, elaidic alcohol and erucylic alcohol; branched-chain alcohols, especially 2-ethyl; 1-hexanol, 2-methyl 1-decanol, 2-methyl; 1-dodecanol, 2-methyl 1-tridecanol, 2-methyl; 1-tetradecanol, 3, 7, 11, 15-tetramethyl; 1-hexadecanol, 2, 3, 5, 7-tetramethyl; 1-nonanol, 2, 4, 7-trimethyl; 1-nonanol, 2-octyl; 1-dodecanol and 2-hexyl-1-decanol. The above-mentioned alcohols can be used in the pure state or in mixtures of isomers or homolog derivatives such for example as fatty alcohols derived from animal or vegetable oils and fats (copra or lard, for example); linear chain alcohols obtained by the "Alfol" process; and fatty alcohols obtained by the "Oxo" process. Among the industrial mixtures that are presently usable there may be mentioned alcohols from tripropylene or tetrapropylene; fatty alcohols prepared by the "Guerbet" reaction; fatty alcohols prepared from fatty acids modified as in U.S. Pat. No. 2,812,342; and mixtures of synthesis alcohols containing about 75% straight chain homologs and 25% two-position alkyl isomers. It is also possible to use as primary material alkyl phenols and especially p-tert-octyl-phenol, p-sec-octyl phenol, p-isononyl phenol, p-tert-dodecyl phenol, p-isododecyl phenol as well as products of the alkylation of phenols by olefins such as dodecene, tripropylene, tetrapropylene and di-isobutylene. Aliphatic or alicyclic high molecular weight alcohol derivatives can also be used, e.g., cerylic alcohol, melissic alcohol, cholesterol, cholestanol, lanosterol, dihydroanosterol, mixtures obtained by catalytic hydrogenation of lanolin or mixtures derived from fatty resin acids and fatty alcohols derived from cyclic fatty acids and represented by the following formulae:

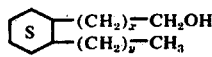

and

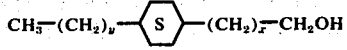

in which formulae $x + y = 10$, and

represents the cyclohexyl radical.

In a preferred embodiment of the process of the preparation of compounds of formula (I) according to the invention, the condensation of the polyhalogenated polyethers with the mercaptan is effected in the presence of an alkali metal hydroxide, preferably in the presence of sodium or potassium hydroxide. These hydroxides are introduced into the reaction medium either pulverized or in the form of a concentrated aqueous solution in close to stoichiometric proportion to the halogen atoms of the polyhalogenated polyethers. Under these conditions, alkaline mercaptides are formed "in situ". It is obvious that it would also be possible to use alkali metal mercaptides for the reaction instead of mercaptans, the said mercaptides being prepared from mercaptans according to known processes by the action of alkali metals or alkali alcoholates.

The condensation reaction of the mercaptan can also be effected in a solvent medium, dissolving or dispersing the reagents in this medium which improves the miscibility of the polyhalogenated polyethers with the alkaline derivatives of the mercaptan. The solvent can advantageously be a lower alcohol such as methanol, ethanol, isopropanol, tertiary butyl alcohol or even a glycol ether such as 2-methoxy-ethanol or 2-ethoxyethanol.

It is preferred that the amount of the mercaptan be of the order of one mole per gram-atom halogen of the polyhalogenated polyether. When the process is carried out at atmospheric pressure with a volatile mercaptan such as methyl mercaptan, there can be loss through evaporation so that the amount of mercaptan utilized can be substantially higher. It is preferable, in such a case, to work in an autoclave.

The condensation reaction of the process according to the invention is rapid and exothermic. It is effected at a temperature between 20° C and 150° C, preferably between 30° C and 110° C. Usually, to obtain practically quantitative levels of transformation, a few hours are sufficient. The course of the reaction is followed by measurements of alkalinity and of the thiol functions in the reaction medium.

The reaction produces an alkali metal halide as a by-product which can be filtered out of the reaction medium, possibly with dilution of the reaction mixture, or even by washing with water.

The compounds obtained by the condensation reaction of the mercaptans with the polyhalogenated polyethers have present, in the oxyalkylene units of the various molecules, substituents of which at least 80% are alkylthio methyl groups, the rest being halogen atoms that have not reacted or hydroxyl groups resulting from hydrolysis involving the halogen atoms of the halogenated substituents. When these compounds are subjected to an oxidation treatment, at least part of the alkylthio groups are converted to alkyl-sulfinyl groups. This oxidation is effected preferably by hydrogen peroxide in the form of an aqueous solution containing 30–35% by weight $H_2O_2$, the amount of $H_2O_2$ being stoichiometric or slightly less than stoichiometric relative to the polythioether groups that were originally present. This oxidation is effected at a temperature between 0° C and 50° C, preferably between 30° C and 40° C. It is effected, preferably, without addition of solvent, and eventually, in the presence of acetic acid in amounts of 0.1 to 1% by weight relative to the total reaction mass.

an attempt has been made to prepare compounds of formula (I) of the invention by a different process which relies on polyaddition of 3-(alkyl-thio)-1,2-epoxy-propane of formula:

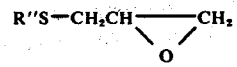

in which R'' is an alkyl, such as a methyl, to a hydroxyl compound of the formula (ROH) in the presence of an alkaline catalyst. This process permits production of compounds of formula (I) but it is much less satisfactory than the process described above.

The present invention also relates to compositions which can be used especially in pharmacy, in cosmetics or as a cleansing agent, the compositions being characterized essentially by the fact that they comprise, in an aqueous or non-aqueous medium, at least one compound of formula (I) present in amounts of about 0.1% to 25% by weight of said composition.

The compositions of the invention may also comprise various ingredients customarily used in pharmacy, cosmetics or in cleansing agents. In particular, the compositions of the invention may comprise, in mixture with compounds of formula (I), other anionic, cationic or non-ionic surfactant compounds.

The properties of a mixture of compounds of formula (I) prepared by the process of the invention depend on the various substituents on the polyether chain, on the value of parameter $m$ which fixes the average degree of polymerization of the oxyalkylene units in the compounds of formula (I), and on the nature of lipophilic radical R. It can be indicated in general, however, that if radical R contains less than 16 carbon atoms, the mixtures that are obtained are more especially useful as foaming agents, and that if radical R has more than 16 carbon atoms, the mixtures that are obtained are more especially useful as emulsifiers. Independently of foaming or emulsifying properties, the compounds of formula (I) can have additional characteristics that make them valuable as wetting agents, gelling agents, detergents or colloiding agents.

It is pointed out that the compounds of formula (I), in which Z represents alkylthio groups, are less hydrophilic than are the corresponding compounds of formula (I) which have undergone an oxidation phase to transform the polythioethers into polysulfoxides. However, certain polythioethers of the formula (I) with dihydroxypropyl radicals are water-soluble.

The compounds of formula (I) which have undergone an oxidation phase in the course of their preparation, i.e., the polysulfoxides, are very hydrophilic, this characteristic depending both upon the value of parameter $m$ and upon the nature of the R' radicals bonded to the sulfoxide group. In general, for values of m between 1 and 5, the polysulfoxides of formula (I) are water-soluble, even at high temperatures and in the presence of electrolytes.

When the radical R contains 12 to 14 carbon atoms and R' is a hydroxyethyl or dihydroxypropyl radical, the compounds of formula (I) are remarkable foaming agents. This fact is very interesting since the non-ionic surfactants heretofore known generally have had poor foam-generating capabilities. The dihydroxypropyl derivatives are moreover devoid of aggressivity to the mucosa of the eye as has been demonstrated in tests on rabbits. Moreover, this characteristic subsists when they are used in a mixture with cationic surfactants. They are, therefore, especially suited for the preparation of hair shampoos.

Some compounds of formula (I) in which R is a radical derived from oleyl alcohol allow production of gelled aqueous solutions and can therefore be used as a support or carrier for conventional hair dyes.

For better understanding of the invention, there are now described as non-limitative illustrations, some examples of preparation and use of these compounds, especially in compounds concerned in cosmetics, pharmacy and in cleansing agents.

EXAMPLE 1

Preparation of a mixture of compounds corresponding to formula (I) wherein R is an aliphatic radical containing 12 to 14 carbon atoms, Z is

and $n$ has an average statistical value of 2.

First phase — Preparation of the Polythioether:

80 g of 40% of NaOH are added to 30 ml absolute ethyl alcohol and a fast flow of methyl mercaptan is bubbled through it. The reaction is exothermic. The temperature reaches 45° C. 39 g of methyl mercaptan are thus dissolved. The reaction mass is heated to 50° C and 153 g of a telomer with 2 moles epichlorhydrin of a mixture of dodecanol and tetradecanol are added dropwise in the course of 20 minutes. The reaction mass is heated to 75° C for 3 hours. After 3 hours of heating, the excess methyl mercaptan and alcohol are driven off under vacuum. The reaction mass is then washed with 120 ml hot water and the aqueous phase is decanted. The level of reaction, according to the chloride content of the aqueous phase, and thioether index of the organic phase, is 87%.

The telomer used in this example was prepared in the following way. To 396 g (i.e., 2 moles) of a mixture of fatty alcohols containing essentially dodecanol and tetradecanol, there are added 1.6 ml of the complex of boron fluoride with acetic acid. Then at 75° C – 80° C there are added 277 g of epichlorhydrin. Heating is maintained for 1 hour after the addition.

Second phase — Preparation of the Polysulfoxide:

To 100 g of thioether obtained in the first phase (i.e., 0.43 mole), there are added 0.5 ml acetic acid and 37.7 ml hydrogen peroxide (130 volumes) dropwise at 30° C to 35° C. The desired polysulfoxide is obtained.

This polysulfoxide is water soluble. Its Kraft point of a 1% solution is 12° C. Its turbidity point at a concentration of 0.5% is 55° C in demineralized water and 36° C in saline water with 10% NaCl.

Applied to the eyes of rabbits, the 4.5% solution with pH 7 is not irritating.

It is pointed out that the compound can also be prepared by polyaddition of 3-methylthio-1,2-epoxy-propane to fatty alcohol in the presence of tetramethyl butane diamine at a temperature of 140° C – 150° C.

EXAMPLE 2

Preparation of a compound corresponding to formula (I) in which R is the aliphatic radical, $C_{12}H_{25}$, Z is

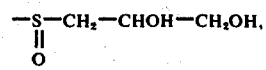

and $n$ has an average statistical value of 1.

First phase — Preparation of the Polythioether:

Starting with the telomer of 1.1 mole epichlorhydrin and lauryl alcohol prepared as indicated in Example 1, which telomer is fractionated by distillation, the monocondensation product is separated, and treated with an excess of 40% aqueous sodium hydroxide in the presence of tertiary butyl alcohol. After separation of the sodium chloride and distillation of the tertiary butyl alcohol, the dodecyl glycidyl ether is distilled at a temperature of 115° C – 117° C under 0.1 mm mercury pressure.

Under nitrogen, there are added, at 90° C to 100° C, 242 g (i.e., 1 mole) of the said dodecyl glycidyl ether to 108 g of thioglycerol in the presence of 1.8 ml triethylamine. The reaction is very fast and the product after cooling has the form of a wax. A polythioether is thus obtained.

Second phase — Preparation of the Polysulfoxide:

150 ml acetone and 2 ml acetic acid are added to the above product and oxidation is effected at 35° C by 88.8 ml peroxide at 126 volumes. When oxidation is terminated, acetone is added, the product is filtered and the polysulfoxide is dried. The product is isolated as a white powder exhibiting a melting point of 77° C.

This product is not wholly soluble in water. At 35° C foam heights measured in a Ross-Miles apparatus, for concentrations of 0.5%, 2% and 5% are, respectively, 2 cm, 3.5 cm and 9.5 cm.

EXAMPLE 3

Preparation of a compound of formula (I) in which R is an aliphatic radical containing 12 to 14 carbon atoms, Z is

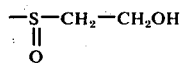

and $n$ has an average statistical value of 2.

First phase — Preparation of the Polythioether:

Sodium mercaptide is prepared by addition, under nitrogen, of 60 g of 40% NaOH to 46.8 g mercapto ethanol (i.e., 0.6 mole). The reaction is exothermic. 50 ml absolute ethyl alcohol are added and there are then introduced in the course of 30 minutes at 80° C 115 g of telomer with 2 moles epichlorhydrin of the mixture of dodecyl and tetradecyl alcohols. After 3 hours of reflux heating, there is 96% reaction. The level of reaction is determined by the alkalinity index and the free mercaptan index. The reaction mass is taken up with 100 ml water at 75° C which produces two liquid phases. After decanting and separation of the aqueous phase, the organic phase is dried under vacuum at 90° C. A little more sodium chloride precipitates which is then filtered out. The thioether thus obtained is a colorless perfectly limpid oil.

Second phase — Preparation of the Polysulfoxide:

1.5 ml acetic acid are added and then, dropwise, at 35° C, 53 ml hydrogen peroxide, at 126 volumes. The reaction is very exothermic. There is a substantial production of foam, and the medium swells enormously. The temperature is held at 35° C throughout the whole addition. After about 15 hours standing, the reaction is practically ended and the foam has completely disappeared.

The polysulfoxide obtained has the form of a very consistent transparent gel. Its Kraft point is below 0° C and the turbidity point is above 100° C in demineralized water and in saline water.

When applied to the eyes of rabbits, a 6.4% solution with pH 7 is very slightly irritating.

Foam measurements with a Ross-Miles apparatus at concentrations of 0.5%, 2% and 5% at 35° C gave, respectively, heights of 17 cm, 19.5 cm and 19 cm.

EXAMPLE 4

Preparation of a mixture of compounds of formula (I) in which R is an aliphatic radical with 12 to 14 carbon atoms, Z is

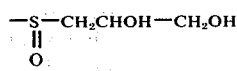

and $n$ has an average statistical value of 1.5.

First phase — Preparation of the Polythioether:

To 162 g thioglycerol (i.e. 1.5 mole) there are added under nitrogen, in the course of 10 minutes, 150 g of 40% NaOH. The reaction is exothermic and the temperature rises to 75° C – 80° C. There are then introduced 100 ml absolute ethyl alcohol and then in the course of 30 minutes 335 g of a telomer with 1.5 mole epichlorhydrin of the mixture of dodecyl and tetradecyl alcohols. Heating is continued for 3 hours at 85° C. The conversion is of the order of 95 to 97% according to a determination of free mercaptan and the alkalinity index. After distillation, at ordinary pressure and then under vacuum, of the alcohol and water, and addition of 50 g of ethoxyethanol, the product is taken up with 200 ml acetone to separate the sodium chloride, which is filtered. After distillation of the acetone, there is obtained a polythioether in the form of a slightly colored translucent gel in which the thioether concentration can be measured to confirm the amount of conversion.

Second phase — Preparation of the Polysulfoxide:

The thioether is oxidized after having added 2 ml acetic acid by dropwise addition at 35° C – 40° C with 130 ml hydrogen peroxide at 126 volumes.

A white paste is thus obtained which, for a concentration of 1%, has a Kraft point of 28° C. At 0.5% the turbidity point is above 100° C, both in demineralized water and in saline water containing 10% NaCl.

Measurements of the foam height with the Ross-Miles apparatus at 35° C at concentrations of 0.5%, 2% and 5% gave, respectively, 15 cm, 18.5 cm and 20.5 cm.

Eye tests on rabbits with 4.7% concentration and pH 7 show that the composition thus prepared can be regarded as non-irritating.

EXAMPLE 5

Preparation of a mixture of compounds of formula (I) in which R is an aliphatic radical with 12 to 14 carbon atoms, Z is

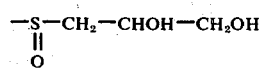

and $n$ has an average statistical value of 2.

First phase — Preparation of the polythioether:

Under nitrogen, to 65 g of thioglycerol (i. e., 0.6 mole) there are added 60 g of 40% NaOH to prepare the sodium mercaptide. The temperature is allowed to rise to 80° C and 35 ml absolute alcohol are introduced. Then in the course of thirty minutes, 115 g of telomer with 2 moles epichlorhydrin of a mixture of dodecyl and tetradecyl alcohols prepared as in Example 1 are added. After 3 hours of reflux heating, 95% reaction is obtained as shown by determination of alkalinity and of residual mercaptans. 40 ml of ethoxyethanol are added, followed by distillation at ordinary pressure, then under vacuum, of the alcohol and water. 100 ml of ethoxyethanol are added and the sodium chloride is filtered, the solvent then being eliminated by distillation under vacuum.

The polythioether that is obtained is in the form of a clear yellow oil of considerable viscosity. It dissolves in water with light opalescence. In 1% concentration it has a Kraft point of 15° C. The turbidity point, which is relatively low, measured in 0.5% concentration in demineralized water, is 35° C.

Second phase — Preparation of the Polysulfoxide:

The polythioether thus obtained is subjected to oxidation in the presence of 0.5 ml acetic acid by dropwise addition, at 35° C of 53 ml hydrogen peroxide at 126 volumes.

The product obtained has a Kraft point of 23° C and a turbidity point above 100° C in both demineralized water and in saline water, 10% NaCl.

Height measurements of the foam in a Ross-Miles apparatus gave for concentrations of 0.5%, 2% and 5%, respectively, 12.5 cm, 14 cm and 17.5 cm.

EXAMPLE 6

Preparation of a mixture of compounds of formula (I) in which R is a radical derived from oleic acid, Z is

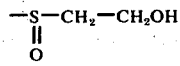

and $n$ has an average statistical value of 2.

First phase — Preparation of the Polythioether:

To 78 g of mercapto ethanol (i.e., 1 mole) there are added, under nitrogen, 100 g of 40% NaOH and then 50 ml absolute ethyl alcohol. Then in the course of thirty minutes 222 g (i.e., 0.5 mole) telomer with 2 moles epichlorhydrin of oleyl alcohol prepared as in Example 1 are added. After the addition, the reaction mixture is heated to 85° C – 90° C for 3 hours. There is then a conversion of 95%. 125 ml of hot water are added to dissolve completely the salt that has formed, which brings about a separation of phases. The organic phase is dried by vacuum evaporation.

Checking of the conversion is also possible by a determination of the chloride ion in the aqueous phase.

Second phase — Preparation of the Polysulfoxide:

To the oil that has been obtained, there are added 1 ml acetic acid and then dropwise between 35° and 40° C, 88.5 ml H$_2$O$_2$ at 126 volumes. After about 15 hours at ambient temperature, the reaction ends and the product has the form of a yellow paste of rather soft consistency.

In water, the product presents a very slight opalescence. It has the property of yielding gels even in weak concentrations in demineralized water and in saline water, 10% NaCl. At a concentration of 0.5% the turbidity points are, respectively, 40° C and 24° C.

At 5% concentration and pH 7, it is absolutely non-irritating to the eyes of rabbits.

EXAMPLE 7

Preparation of a mixture of compounds of formula (I) in which R is the oleyl radical, Z is

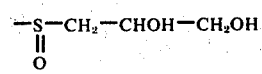

and $n$ has an average statistical value of 2.

First phase — Preparation of the Polythioether:

To 108 g of thioglycerol (i.e., 1 mole) there are added, under a nitrogen atmosphere, 100 g of 40% NaOH. The reaction is strongly exothermic and the temperature reaches 75° C. There are then added 100 ml absolute ethyl alcohol and then, in the course of thirty minutes, 222 g (i.e., 0.5 mole) of a telomer of oleyl alcohol with two moles epichlorhydrin prepared as in Example 1. The temperature is then held at 85° C – 90° C for 3 hours. After dilution with 75 ml water and 150 ml tertiary butyl alcohol, the major part of the aqueous phase and the chlorides are separated, followed by vacuum distillation of the tertiary butyl alcohol and residual water.

The polythioether thus obtained has the form of a light yellow paste.

Second phase — Preparation of the Polysulfoxide:

The polythioether that has been obtained is oxidized by dropwise addition of 88.5 ml hydrogen peroxide at 126 volumes in the presence of 1 ml acid at a temperature of 35° C.

The polysulfoxide is perfectly soluble in water. The Kraft point for 1% concentration is below 0° C. The turbidity point for a 0.5% solution in demineralized water and in saline water, 10% NaCl, is above 100° C.

A 6% solution applied to the eyes of rabbits shows absolutely no irritation.

EXAMPLE 8

Preparation of a mixture of compounds of formula (I) in which R is an aliphatic radical containing 16 to 18 carbon atoms, Z is

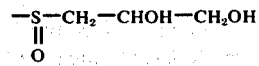

and $n$ has an average statistical value of 1.8.

First phase — Preparation of the polythioether:

To 66 g of thioglycerol (i.e., 0.6 mole) there are added, under nitrogen, 60 g of 40% NaOH. The temperature is increased to 80° C and 35 ml absolute ethyl alcohol are introduced and then in the course of 30 minutes 114 g of a telomer of 1.8 mols epichlorhydrin and cetylstearyl alcohol are added. The temperature is held at reflux for 3 hours. The alcohol and water are driven off under vacuum, with the addition of 25 ml of ethoxyethanol to prevent foaming. The product is taken up in absolute ethyl alcohol and the sodium chloride that has formed is filtered off.

Second phase — Preparation of the Polysulfoxide:

One ml of acetic acid is added and, at 35° C, 53 ml hydrogen peroxide are added. After distillation of the alcohol, there is obtained a white water-soluble paste. The polysulfoxide that is obtained has a Kraft point of 47° C for a 1% solution and a turbidity point above

EXAMPLE 9

Preparation of a mixture of compounds of formula (I) in which R is stearyl polyoxypropylene, the degree of polymerization 5.25, Z is

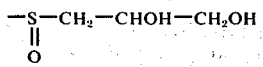

and $n$ has an average statistical value of 2.

First phase — Preparation of the Polythioether:

The sodium mercaptide of thioglycerol is prepared and isolated. To do this, there are added to 108 g of 2,3-dihydroxypropyl mercaptan, under nitrogen, 100 g of 40% NaOH. The reaction is strongly exothermic. The product is cooled and taken up in acetone, filtered and dried. The mercaptide thus prepared is a white crystallized product, titering 82% free mercaptans, the remainder being essentially volatile products.

116 g of a chlorinated ether derivative prepared as in Example 1 are heated with 50 ml absolute ethyl alcohol to 50° C under nitrogen. In the course of 5 minutes, 48 g (i.e., 0.3 mole) of the sodium mercaptide are added and the mixture is placed under reflux. The temperature is held at reflux for 3 hours. There is then a conversion of 93 – 94%. The mixture is diluted with 80 ml absolute ethyl alcohol and the sodium chloride is filtered.

Second phase — Preparation of the Polysulfoxide:

The polythioether is subjected to oxidation in an ethyl alcohol medium in the presence of 1 ml acetic acid with 26.6 ml hydrogen peroxide at 126 volumes, at a temperature of 35° C. Distillation of the alcohol under vacuum follows. The product thus obtained can be dispersed in water and thus can be used as an emulsifier. For example, with 10 g of this compound, 30 g paraffin oil and 60 g water, there is obtained an oil-in-water emulsion which is stable for several days at a temperature of 35° C.

EXAMPLE 10

Preparation of a mixture of compounds of formula (I) in which R is an aliphatic radical derived from lanolin alcohol, Z is

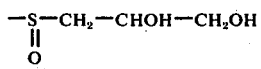

and $n$ has an average statistical value of 2.

First phase — Preparation of the Polythioether:

To 138.5 g (i.e., 0.25 mole) of a telomer with 2 moles epichlorhydrin of lanolin alcohol, prepared by catalytic hydrogenation, there are added 75 ml of absolute ethyl alcohol and then 79 g (i.e., 0.5 mole) sodium mercaptide prepared as in Example 9. The mixture is refluxed for 3 hours followed by dilution with 100 ml absolute ethyl alcohol and filtering of the sodium chloride.

Second phase — Preparation of the Polysulfoxide:

To the filtrate there is added 1 ml acetic acid, and oxidation is effected at 35° C by addition of 44.4 ml $H_2O_2$ at 126 volumes. When the oxidation is ended, the alcohol is driven off under vacuum and the remainder is then heated to 90° C – 100° C for 5 minutes. The product thus obtained presents a slight opalescence in water.

EXAMPLE 11

Preparation of a mixture of compounds of general formula (I) in which R is an aliphatic radical derived from lanolin alcohol, Z is $-S-CH_2-CHOH-CH_2OH$ and $n$ has an average statistical value of 5.

To 124.5 g of telomer with 5 moles epichlorhydrin of the product known commercially under the trademark "Hydrolan" (fatty alcohols of lanolin obtained by catalytic hydrogenation) there were added under nitrogen atmosphere 100 ml absolute ethyl alcohol and then at 50° C 119.5 g of sodium mercaptide prepared as in Example 9. The reaction mass was then refluxed for 5 hours. The conversion was then 94%.

The mixture was diluted with 100 ml absolute ethyl alcohol and the sodium chloride was filtered. After vacuum distillation, there was obtained a polythioether which was a brown water-soluble product whose Kraft point is below 0° C and whose turbidity point is above 100° C (in demineralized water and in saline water).

EXAMPLE 12

Preparation of a mixture of compounds of formula (I) in which R is a nonyl-phenyl radical, Z is

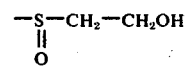

and $n$ has an average statistical value of 4.5.

First phase — Preparation of the Polythioether:

To 95 g of the telomer of nonyl-phenol, with 4.5 moles epichlorhydrin, there are added under nitrogen 53 g of thioethanol (i.e., 0.66 mole) and 66 g of 40% NaOH. The mixture is heated for 90 minutes at 100° C. There is separation into two phases. 50 ml absolute ethyl alcohol are then added and the mixture is heated at reflux for 2 more hours. By addition of 75 ml of water at 75° C, the sodium chloride is completely dissolved and there are always two liquid phases.

Second phase — Preparation of the Polysulfoxide:

The aqueous phase is separated, and after dilution of the organic phase with 50 ml of ethyl alcohol, oxidation is effected by dropwise addition of 55 ml of hydrogen peroxide at 126 volumes. After the reaction is completed, the alcohol and part of the water are vacuum distilled off. The polysulfoxide is soluble in water and its turbidity point is above 100° C in demineralized water and in saline water containing 10% NaCl.

EXAMPLE 13

Preparation of a mixture of compounds of formula (I) in which R is a 2-octyl dodecyl radical, Z is

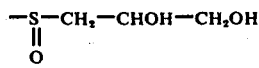

and $n$ has an average statistical value of 4.5.

First phase — Preparation of the Polythioether:

50 ml of absolute ethyl alcohol are added to 72 g of a telomer of 2-octyl dodecanol with 4.5 moles epichlorhydrin, and then, under nitrogen atmosphere at 50° C, there are added 71.5 g of sodium mercaptide of thioglycerol (i.e., 0.45 moles) prepared as in Example 9. After three hours of reflux heating, the mixture is diluted with 50 ml of absolute ethyl alcohol and the sodium chloride is filtered off.

Second phase — Preparation of the Polysulfoxide:

Oxidation is carried out at 35° C after addition of 1 ml acetic acid with 40 ml of hydrogen peroxide at 126 volumes. After distillation of the alcohol under vacuum, there is obtained polysulfoxide as a clear water-soluble yellow gel.

EXAMPLE 14

Preparation of compounds having the formula:

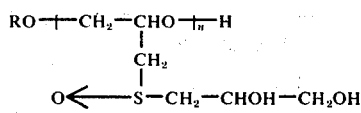

wherein R is the hydrocarbon residue from Dobanol 25 containing 12–15 carbon atoms and $n$ has an average statistical value of 1.5.

First phase — Preparation of the Polythioether:

To 174.5 g (0.5 mole) of a telomer derived from Dobanol 25 and 1.5 mole of epichlorohydrin in 75 ml of absolute ethyl alcohol there are added at a temperature of 60° C and under a nitrogen atmosphere, 118 g of sodium mercaptide of thioglycerol (0.75 mole) prepared as in Example 9. The reaction mass is heated to reflux for 2½ hours, the amount of transformation being about 96%. The reaction mass is then diluted with 55 ml of absolute ethanol and filtered. After distillation of the solvent under reduced pressure, there is obtained the thio ether in the form of a paste.

Second phase — Preparation of the Polysulfoxide:

To 200 g of the thioether thus prepared, there are added 1 ml of acetic acid and then at a temperature of 30° C to 35° C, 57.5 ml of $H_2O_2$ (at 126 volumes). The resulting polysulfoxide is a paste, soluble in water, having a Kraft point of 20° C – 24° C, and a cloud point greater than 100° C in demineralized water and 67° C in water containing 10% sodium chloride.

Foam heights measured with a Ross and Miles apparatus for concentrations of 0.5%, 2% and 5% are, respectively, 7 cm, 12.5 cm and 15 cm.

EXAMPLE 15

Preparation of compounds having the formula:

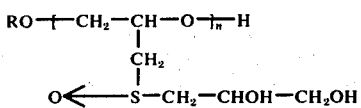

wherein R is a mixture of alkyls having 8 – 10 carbon atoms (the hydroxyl index of which is 380) and n has an average statistical value of 1.5.

First phase — Preparation of the Polythioether:

At a temperature of 60° C there are added to 2 moles (30.2 g) of an alcohol containing 8 to 10 carbon atoms, 1.6 ml of a boron trifluoride complex in acetic acid solution. At 70° C, 27.75 g (0.3 mole) of epichlorhydrin are added dropwise, this addition being carried in a manner such that the temperature does not exceed 80° C. The reaction is exothermic and the addition lasts for 45 minutes. The mixture is then stirred for one additional hour at the same temperature.

Sodium mercaptan of thioglycol is then prepared by mixing under a nitrogen atmosphere at ambient temperature 36.2 g (0.3 mole) of thioglycol and 30 g of 40% NaOH. The reaction is exothermic and the temperature rises to 65° C. At the end of the addition to the white powder thus obtained there are added 20 ml of absolute ethyl alcohol. Then at a temperature between 75° C and 80° C there is added the telomer prepared as described above, this addition lasting for ½ hour. The reaction mixture is heated for 5 hours at 85° C and thereafter the alcohol solution is eliminated by evaporation. There is obtained a chestnut colored gel.

Second phase — Preparation of the Polysulfoxide:

There is then added to this chestnut gel, 0.4 ml of acetic acid. This mixture is heated between 35° C and 45° C and at this temperature there is added little by little 25.1 ml of $H_2O_2$ (at 127 volumes). The reaction is very exothermic and the addition lasts for 40 minutes. The reaction mixture is maintained at a temperature of 35° C to 45° C for nine hours. The chestnut paste thus obtained is placed in a dessicator to dry in order to eliminate water resulting from the decomposition of $H_2O_2$.

The resulting polysulfoxide, in paste form, is soluble in water. The cloud point of this paste is determined by preparing a 5% solution in an aqueous mixture of 25% butyl diglycol. In this mixture, the cloud point remains above 96° C; that is to say the solution remains clear even after heating in a boiling bath.

The cloud point of this same paste has also been determined in an aqueous solution and in a solution of water to which has been added sodium chloride, these tests being made at a concentration of 0.5%.

The solutions remain clear in demineralized water and in water to which has been added sodium chloride which proves that the cloud point is greater than 96° C.

EXAMPLE 16

A composition was prepared by mixing:

| | |
|---|---|
| Mixture of sulfoxide compounds prepared as in the second phase of Example 3 | 15 g |
| N,N-diethanol lauramide | 2 g |
| Carboxymethylcellulose | 0.2 g |
| Water in sufficient quantity for | 100 g |

The composition has a pH of 7 and can be used as hair shampoo.

EXAMPLE 17

A composition was prepared by mixing:

| | |
|---|---|
| Mixture of sulfoxide compounds prepared as in the second phase of Example 4 | 7 g |
| Trimethyl-cetyl-ammonium bromide | 3 g |
| Lactic acid sufficient to adjust to pH 3 | |
| Water in sufficient quantity for | 100 g |

This composition can be used as hair shampoo.

EXAMPLE 18

A composition was prepared by mixing:

| | |
|---|---|
| Mixture of sulfoxide compounds prepared as in the second phase of Example 3 | 4 g |
| Trimethyl-cetyl-ammonium bromide | 3 g |
| Condensate of lauryl alcohol with 12 | |

-continued

| | |
|---|---|
| moles of ethylene oxide | 5 g |
| N,N-diethanol lauramide | 1.5 g |
| Lactic acid in sufficient quantity to reduce to pH 5 | |
| Water in sufficient quantity for | 100 g |

This composition can be used as hair shampoo.

EXAMPLE 19

A composition was prepared by mixing:

| | |
|---|---|
| Mixture of sulfoxide compounds prepared as in the second phase of Example 4 | 10 g |
| Sodium salt of $N^1$-($N'$,$N'$-dimethylamino-propyl-$N^2$-alkyl-(copra)-asparagine | 3 g |
| Lactic acid in sufficient quantity to adjust to pH 3 | |
| Water in sufficient quantity for | 100 g |

This composition can be used as hair shampoo.

EXAMPLE 20

A composition was prepared by mixing:

| | |
|---|---|
| Mixture of sulfoxide compounds prepared as in the second phase of Example 3 | 8 g |
| Sodium N-lauryl-beta-iminopropionate | 3 g |
| Trimethyl-cetyl-ammonium bromide | 2 g |
| Lactic acid in sufficient quantity to adjust to pH 6 | |
| Water in sufficient quantity for | 100 g |

This composition can be used as hair shampoo.

EXAMPLE 21

A composition was prepared by mixing:

| | |
|---|---|
| Mixture of sulfoxide compounds prepared as in the second phase of Example 4 | 5 g |
| Technical triethanolammonium lauryl-sulfate (100%) | 2 g |
| N,N-diethanol lauramide | 2 g |
| Carboxymethylcellulose | 0.3 g |
| Water in sufficient quantity for | 100 g |

This composition can be used as hair shampoo.

EXAMPLE 22

COLORING SHAMPOO

A composition was prepared by mixing:

| | | |
|---|---|---|
| Condensate of lauryl alcohol with 4 moles of ethylene oxide | 10 | g |
| Condensate of lauryl alcohol with 2 moles of ethylene oxide | 20 | g |
| Ammonium lauryl-sulfate with 30% active substances | 25 | g |
| Mixture of sulfoxide compounds prepared as in the second phase of Example 6 | 2 | g |
| 2-butoxy-ethanol | 5 | g |
| Propylene glycol | 15 | g |
| 20% ammonia | 12 | ml |
| Paratoluolene-diamine base | 0.9 | g |
| Para-aminophenol base | 0.9 | g |
| m-diamino-anisol sulfate | 0.06 | g |
| m-aminophenol | 0.2 | g |
| Resorcinol | 0.5 | g |
| Ethylene diamine tetraacetic acid | 3 | g |
| 40% sodium bisulfite | 2 | g |
| Water in sufficient quantity for | 100 | g |

This composition is mixed weight for weight with hydrogen peroxide to 20 or 30 volumes before use. It is applied to the hair, and a chestnut coloration is obtained. The hair is readily untangled, silky and brilliant.

EXAMPLE 23

BRIGHTENING SHAMPOO

A composition was prepared by mixing:

| | | |
|---|---|---|
| RO$\dashv$C$_2$H$_3$$-$(CH$_2$OH) O$\dashv_2$H in which R is the alkyl radical derived from oleic acid | 5 | g |
| Sodium lauryloxyethylene (2 moles ethylene oxide) sulfate (30% solution) | 25 | g |
| N,N-diethanolamide of cocoanut oil fatty acid | 12 | g |
| Lauryl alcohol | 2 | g |
| Mixture of sulfoxide compounds prepared as in the second phase of Example 7 | 2 | g |
| 2-butoxy-ethanol | 4 | g |
| Propylene glycol | 8 | g |
| 20% aqueous ammonia | 5 | ml |
| Water in sufficient quantity for | 100 | g |

Before use this composition is mixed, weight for weight, with 20 volumes hydrogen peroxide. After an interval of 30 minutes, there is a 2 to 2½ tone brightening. The hair is readily untangled. The feel is very silky.

EXAMPLE 24

A composition is prepared by mixing:

| | | |
|---|---|---|
| Ester of fatty acid of copra with sodium isothionate | 70.5 | g |
| Mixture of compounds prepared according to Example 4 | 2.5 | g |
| Stearic acid | 17 | g |
| Water, q.s.p. | 10 | g |

One mixes the above components and passes the mixture twice in a cylindrical mill where it is extruded and cut and pressed into cakes to give it its customary form. One obtains, thus, a dermatological detergent cake, exhibiting advantageous foaming power characteristics.

EXAMPLE 25

A composition is prepared by mixing:

| | | |
|---|---|---|
| Mixture of compounds prepared in Example 2 | 10 | g |
| Nonylphenol oxyethylenated with 9 moles of ethylene oxide | 20 | g |
| Diethanolamide of coco | 10 | g |
| Butylglycol | 5 | g |
| Propylene glycol | 17 | g |
| Ammonia, at 22° Be | 12 | ml |
| Meta-diamino anisol sulfate | 0.03 | g |
| Resorcinol | 0.40 | g |
| Meta-amino-phenol | .15 | g |
| Para-aminophenol | 0.087 | g |
| Nitro-paraphenylene diamine | 0.004 | g |
| Paratoluylene diamine | 1 | g |
| Ethylene diamine tetraacetic | 2 | g |
| Sodium bisulfite (d = 1.32) | 1.200 | ml |

| | |
|---|---|
| Water, q.s.p. | 100 g |

There is mixed by weight, an equal part of the above composition with a part of $H_2O_2$ at 20 volumes. The resulting mixture is then applied to the hair to obtain a foam and it is left there for 30 minutes. Thereafter the hair is rinsed with water and a chestnut brown coloration is obtained. The same satisfactory result can be obtained by replacing the mixture of compounds prepared according to Example 2 by the same quantities of the mixture of compounds prepared according to Example 13.

EXAMPLE 25

A composition is prepared by mixing:

| | |
|---|---|
| Mixture of compounds prepared in Example 12 | 10 g |
| Nonylphenol oxyethylenated with 4 moles of ethylene oxide | 30 g |
| Butylglycol | 6 g |
| Propylene glycol | 10 g |
| Ammonia (22° Be) | 12 ml |
| Resorcinol | 0.04 g |
| Meta-aminophenol | 0.06 g |
| Para-aminophenol | 0.28 g |
| Nitro-paraphenylene diamine | 0.02 g |
| Paratoluolene diamine | 0.12 g |
| Hydroquinone | 0.17 g |
| Ethylene-diamine tetraacetic acid | 3 g |
| Sodium bisulfite (d = 1.32) | 0.80 ml |
| Water, q.s.p. | 100 g |

There is thus obtained a hair dye composition in gel form. To one part of the above defined dye composition there is mixed one part of $H_2O_2$ at 20 volumes. The resulting mixture is applied to the hair and is permitted to remain in contact therewith for 30 minutes. The hair is then rinsed with water and there is thus obtained on bright chestnut hair a golden blonde coloration.

EXAMPLE 26

A composition is prepared by mixing:

| | | |
|---|---|---|
| Mixture of compounds prepared according to Example 8 | 5 | g |
| Stearyl alcohol | 20 | g |
| Sodium cetyl-stearyl sulfate | 3 | g |
| Diethanolamide of coco | 4 | g |
| Ammonia (22° Be) | 10 | ml |
| Meta-diamino anisol sulfate | 0.048 | g |
| Resorcinol | 0.420 | g |
| Meta-aminophenol | 0.15 | g |
| Para-aminophenol | 0.085 | g |
| Nitro-paraphenylene diamine | 0.004 | g |
| Para-toluylene diamine | 1 | g |
| Ethylene diamine tetra acetic | 1 | g |
| Sodium bisulfite (d = 1.32) | 1.2 | ml |
| Water, q.s.p. | 100 | g |

There is thus obtained a hair dye composition in cream form, the mixture of compounds of Example 8 being used as a thickening agent. In the use of this dye composition, there are mixed 1.5 parts of $H_2O_2$ at 20 volumes with one part of the said composition, the resulting mixture then being applied to the hair and being permitted to remain in contact therewith for 30 minutes.

The hair is then rinsed with water and shampooed. Thereafter it is rinsed again. On white hair a brown coloration is achieved. Essentially the same results can be achieved by replacing the 5 g of the mixture of compounds prepared in accordance with Example 8 by 4 g of the mixture of compounds prepared in accordance with Example 9.

What is claimed is:

1. A composition utilizable in pharmacy, cosmetics or as a cleansing agent comprising in an aqueous or non-aqueous carrier at least one compound of the formula

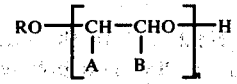

wherein R represents a member selected from the group consisting of alkyl containing 8–30 carbon atoms, alkenyl containing 8–18 carbon atoms, nonyl phenyl, alkyl polyoxyalkylene containing 14–60 carbon atoms and 1–10 oxygen atoms and cycloaliphatic which is the residue of alcohols derived from the hydrogenation of lanolin, one of A and B represents hydrogen and the other a member selected from the group consisting of —$CH_2Z$, halomethyl and hydroxy with the proviso that at least 80% thereof be —$CH_2Z$ wherein Z is selected from the group consisting of R'S- and

wherein R' is selected from the group consisting of alkyl, monohydroxyalkyl and polyhydroxyalkyl, containing 1–4 carbon atoms, and $n$ ranges between 1 and about 20, said compound being present in an amount of 0.1 to 25 percent by weight based on the total weight of said composition.

2. The composition of claim 1 wherein R is selected from the group consisting of alkyl, dodecyl, tetradecyl, cetyl, stearyl, polyoxypropylene stearyl, lanolin alcohol radical, nonyl phenyl and 2-octadodecyl.

3. The composition of claim 1 wherein Z is selected from the group consisting of dihydroxypropyl sulfinyl and hydroxyethyl sulfinyl group.

4. The composition of claim 3 in which at least 80% of the Z group are dihydroxypropyl sulfinyl radicals.

5. The composition of claim 1 which also includes an effective amount of a surfactant other than said compound of claim 1, said surfactant being selected from the group consisting of anionic, cationic and non-ionic surfactants.

6. A composition utilizable in pharmacy, cosmetics or as a cleansing agent comprising in an aqueous or non-aqueous carrier a mixture of compounds having the formula

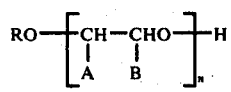

wherein R represents a member selected from the group consisting of alkyl containing 8–30 carbon atoms, alkenyl containing 8–18 carbon atoms, nonyl phenyl, alkyl polyoxyalkylene containing 14–60 carbon atoms and 1–10 oxygen atoms and cycloaliphatic which is the residue of alcohols derived from the hydrogenation of lanolin, one of A and B represents hydrogen and the other a member selected from the group consisting of —CH₂Z, halomethyl and hydroxy with the proviso that at least 80% thereof be —CH₂Z wherein Z is selected from the group consisting of R'S— and

wherein R' is selected from the group consisting of alkyl, monohydroxyalkyl and polyhydroxyalkyl, containing 1–4 carbon atoms and $n$ ranges from 1–10, said mixture of compounds being present in an amount of 0.1 to 25 percent by weight based on the total weight of said composition.

7. A mixture of compounds of the formula

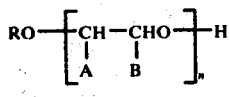

wherein R represents a member selected from the group consisting of alkyl containing 8–30 carbon atoms, alkenyl containing 8–18 carbon atoms, nonyl phenyl, alkyl polyoxyalkylene containing 14–60 carbon atoms and 1–10 oxygen atoms and cycloaliphatic which is the residue of alcohols derived from the hydrogenation of lanolin, one of A and B represents hydrogen and the other a member selected from the group consisting of —CH₂Z, halomethyl and hydroxy with the proviso that at least 80% thereof be —CH₂Z wherein Z is

wherein $R^1$ is selected from the group consisting of alkyl, monohydroxyl alkyl and polyhydroxylalkyl, containing 1–4 carbon atoms and $n$ ranges between 1 and about 20.

8. The compounds of claim 7 wherein Z represents a dihydroxypropyl sulfinyl or hydroxyethyl sulfinyl group.

9. The compounds of claim 7 wherein R is selected from the group consisting of oleyl, dodecyl, tetradecyl, cetyl, stearyl, polyoxypropylene stearyl, lanolin alcohol radical, nonyl-phenyl and 2-octyldodecyl.

* * * * *